United States Patent [19]
Elphingstone et al.

[11] Patent Number: 6,001,158
[45] Date of Patent: Dec. 14, 1999

[54] DRY BIOCIDE

[75] Inventors: Eugene A. Elphingstone, Missouri City; Frank B. Woodworth, Houston, both of Tex.

[73] Assignee: Baker Hughes Incorporated, Houston, Tex.

[21] Appl. No.: 09/253,133

[22] Filed: Feb. 18, 1999

[51] Int. Cl.$^6$ .......................... A01N 25/08; A01N 31/00; A01N 57/00
[52] U.S. Cl. ..................... 106/18.31; 106/18.34; 210/764; 252/175; 422/28; 424/409; 424/417; 424/421; 504/153; 514/126; 514/129
[58] Field of Search ............................ 106/18.31, 18.34; 504/153; 514/126, 129; 422/28; 424/409, 417, 421; 210/764; 252/175

[56] References Cited

U.S. PATENT DOCUMENTS

| | | | |
|---|---|---|---|
| 4,552,591 | 11/1985 | Millar | 106/18.33 |
| 4,673,509 | 6/1987 | Davis et al. | 210/699 |
| 4,775,407 | 10/1988 | Talbot et al. | 504/207 |
| 5,030,358 | 7/1991 | Cooper et al. | 210/670 |
| 5,139,561 | 8/1992 | Talbot et al. | 504/153 |
| 5,385,896 | 1/1995 | Bryan et al. | 514/129 |
| 5,741,757 | 4/1998 | Cooper et al. | 504/153 |

OTHER PUBLICATIONS

Albright & Wilson, "Tolcide PS", Product Bulletin, undated.
Albright & Wilson, "TOLCIDE® PS", Technical Bulletin 235, undated.

*Primary Examiner*—Anthony Green
*Attorney, Agent, or Firm*—Madan, Mossman & Sriram, P.C.

[57] ABSTRACT

A method has been discovered for controlling bacterial growth using a dry biocide. Tetra-kis-hydroxymethyl-phosphonium sulfate (THPS) is adsorbed on a solid, particulate substrate through a spraying technique. The THPS in a dry form eliminates or reduces risks involved in handling and shipping the normally liquid THPS.

12 Claims, 9 Drawing Sheets

DRY BIOCIDE

FIELD OF THE INVENTION

The present invention relates to methods and compositions for inhibiting bacterial growth in fluids, and more particularly relates, in one embodiment, to methods and compositions for inhibiting bacterial growth in oil field fluids using a dry biocide.

BACKGROUND OF THE INVENTION

Bacterial contamination of drilling fluids contributes to a number of problems in the oil field. First, many of the muds contain sugar based polymers in their formulation that provide an effective food source to bacterial populations. This can lead to direct degradation of the mud. In addition, bacterial metabolism can generate deleterious products, most notably hydrogen sulfide that besides being a toxic gas can lead to decomposition of mud polymers, formation of problematic solids, such as iron sulfide, and/or corrosive action on drilling tubes and drilling hardware.

Efforts to control bacterial activity in drilling fluids has been moderately successful. One of the more effective biocides to date is XCIDE 102 (XC 102) sold by Baker Petrolite, a glutaraldehyde-based biocide. However, XC 102 can be problematic because it is hazardous to handle and has environmental concerns.

U.S. Pat. No. 4,552,591 describes a biocide that is a mixture of 5-chloro-2-methyl-4-isothiazolin-3-one and 2-methyl-4-isothiazolin-3-one in a weight ratio of the former to the latter being about 94% to about 64%, adsorbed on a solid, particulate adsorbent. This biocide is sold as XCIDE 207 (XC 207) by Baker Petrolite.

One product that shows potential under these constraints is MAGNACIDE 575. MAGNACIDE 575 or tetra-kis-hydroxymethyl-phosphonium sulfate (THPS) is a quaternary phosphonium salt that can effectively control bacterial growth in a number of systems. MAGNACIDE 575 is available from Aquaness Chemicals (Baker Petrolite) in 75% active liquid form, as well as in a 35% active form. Liquids are difficult to apply in stimulation and drilling applications. Some customers are reluctant to use an expensive liquid such as MAGNACIDE 575 because of potential financial losses due to spills such as may occur during handling and shipping. For instance, it is difficult for a field fracturing operator to climb atop a 20,000 gallon frac tank carrying gallon jugs of liquid biocide. MAGNACIDE 575 has the significant advantage of being "environmentally friendly".

It would thus be desirable to develop a composition and method employing it which did not involve the use of a liquid biocide.

SUMMARY OF THE INVENTION

Accordingly, it is an object of the present invention to provide a dry biocide composition and method for using it.

It is another object of the present invention to provide a method for producing a dry biocide composition.

In carrying out these and other objects of the invention, there is provided, in one form, a method of inhibiting bacterial growth in compositions selected from the group consisting of fluids and solids by adding thereto an effective bacterial inhibiting amount of a biocide comprising tetra-kis-hydroxymethyl-phosphonium sulfate (THPS) adsorbed on a solid, particulate substrate.

DETAILED DESCRIPTION OF THE INVENTION

It has been discovered that tetra-kis-hydroxymethyl-phosphonium sulfate (THPS) loses its activity if it is dried. Instead, it has been surprisingly discovered that THPS can be provided in a dry form if the THPS is sprayed onto a solid, particulate substrate. As will be shown, the THPS does not lose its activity if provided in a dry form in this inventive manner. It is expected that this dry form of THPS will find utility as a biocide in many types of fluids including, but not necessarily limited to, oil field fluids, e.g. drilling fluids, fracturing fluids, fracturing gels, completion fluids, and the like. It is also expected that the dry biocide of this invention would have utility in industrial water treating and oil field chemicals and other chemicals and fluids where bacterial growth was a concern. Because the dry biocide of this invention is in a convenient dry form, it has greater versatility in how it may be added and may be combined with other agents or additives for other purposes prior to its end use.

Indeed, it is possible to produce large volumes of dry powdered product by means of hydraulic spraying of THPS onto a substrate in mixing equipment. It is desired that the THPS be as concentrated as possible. THPS in its 75% active form (commercially available) may be employed, or may be used in a more or less concentrated form. The liquid spray is normally produced at a high pressure so that the product being applied becomes an aerosol. This can be accomplished with a hydraulic spray with an 0.015 inch (0.38 mm) orifice at from about 1800 to 2000 psi, in one non-limiting embodiment. The liquid should be atomized.

The substrate to which the aerosol is applied may be many and varied. Substrates may be insoluble or soluble, organic or inorganic, resinous or non-resinous, depending on the end use and what can be tolerated. The substrate should, of course, be inert with respect to THPS, and the environment into which it is to be inserted. In one non-limiting embodiment of the invention, the solid, particulate substrate may be silica, sodium sulfate, sodium carbonate, sodium chloride, potassium chloride, borax, diatomaceous earth and many other inorganic compounds. Silica is a preferred substrate. As used herein, "silica" is taken to include, but is not necessarily limited to silica gel, either precipitated and/or fumed; silica flour; synthetic amorphous precipitated silica, and the like.

The concentration of the applied product may be from 1–90%, and in certain instances may be applied 100%, based on the material sprayed, prior to applying to the substrate. Production as high as 10,000 lbs or higher per day may be achieved depending on the size of the mixing equipment, in one non-limiting embodiment.

The spray application can be performed in a double ribbon blender or other dry blending equipment. The substrate is added to the blender, and with the blender running, the desired product is added by spraying.

The technique of making the dry biocide of this invention developed in part to combat the high costs of spray drying, and the fact that some organic compounds cannot withstand the high temperatures of spray drying. The temperatures expected for the spraying technique of this invention range from ambient to lower, and up to about 120° F. (49° C.), preferably up to about 80° F. (27° C). The only temperature limitation is the stability of the biocide.

The proportion of THPS on the substrate may range from about 1 to about 90 weight percent, preferably from about 5 to about 80 wt. %.

Without wanting to be limited to any particular explanation, it is believed that an important key to the invention is the fact that the biocide is dried (adsorbed) onto the substrate, rather than dried via dehydration. As noted, dehydration deactivates the biocide.

It is anticipated that the dry biocide of the present invention may find application in a wide variety of compositions, including liquids and solids. Fluids may include, but are not necessarily limited to, drilling fluids, drill-in fluids, completion fluids and other liquids where inhibiting of bacteria growth is desired. The dry biocide will also find utility in frac gels; guar gums; xanthan gums; cellulose gums, such as hydroxyethylcellulose, carboxymethylcellulose, and the like. The dry biocide is also expected to have utility in other viscosified environments. Further, the dry biocide is expected to find utility in solid compositions, including, but not necessarily limited to, powders, plastic explosives, and other solid contexts.

The amount of dry biocide containing THPS used to control or eliminate bacteria in a composition cannot be specified in advance because it depends on a number of factors. Such factors include, but are not limited to, the nature of the composition, for example if it is a fluid, e.g. the nature of the fluid; aqueous, oil-based, emulsion and kind of emulsion, etc.; properties of the fluid, e.g. pH, temperature, contaminants, etc.; e.g. nature and populations of the bacteria to be controlled, etc.; and characteristics of the fluid processing operation, e.g. flow rates, pressures, contact times possible, etc.

The invention will be further described with respect to specific examples which are meant to illuminate the invention and not limit it to any particular embodiment.

EXAMPLE 1

The present inventive product made by the spraying technique described above includes a 75% active solution of THPS adsorbed on a fine silica gel, precipitated and/or fumed. A dry, flowable powder is obtained with approximately 52% active THPS. This is approximately a 2:1 weight mixture, silica:THPS. No exotherm was detected during the spraying and blending.

Considerable additional work was performed to examine the performance of THPS, in both its fluid and dry forms, as a biocide in the drilling fluid XCD polymer. XCD polymer is a xanthan gum-based polymer that is particularly vulnerable to microbial degradation, and was therefore selected to provide a rigorous test of biocidal efficacy. The evaluation was made testing THPS in both in its liquid (MAGNACIDE 575, 75% THPS) and solid (about 50% THPS, as in Example 1) product forms.

Materials and Methods

Bacterial Inoculation

Bacterial cultures were prepared from produced water samples obtained from western Kansas. General aerobic and facultative anaerobic bacteria (GAB) were cultured in Phenol Red Dextrose with 0.5% Total Dissolved Solids (TDS). Sulfate reducing bacteria (SRB) were cultured in an anaerobic media, American Petroleum Institute Recommended Practice No. 38 for SRB (API RP38 SRB) with 0.5% TDS. When sufficient titres of these organisms had been cultured, they were counted using epi-fluorescence microscopy and used to inoculate the respective drilling mud samples in the study.

Bacterial Enumeration

To enumerate the total number of GAM or SRB for the determination of titres present in the stock cultures, samples were prepped and viewed through a Nikon Labophot microscope equipped with a fluorescence epi-illuminator. Samples were prepared by filtering diluted aliquots from stock cultures through black, 25 mm diameter, 0.2 μm pore polycarbonate filters. The bacteria trapped on the filters were stained with acridine orange. Filters were then mounted on microscope slides and analyzed by epi-fluorescence microscopy at 1000× magnification.

Bacterial growth during the study was determined by two methods, agar pour plates for GAB and serial dilution into media vials for SRB. For GAB enumeration, 1 ml of sample mud culture was diluted into 99 mls sterile 0.5% brine, with serial 1:100 dilutions to yield a dilution series of $1:10^2$, $1:10^4$, $1:10^6$, $1:10^8$, and $1:10^{10}$. Subsequently, one ml from each dilution in the series was mixed with 15 ml liquid (50° C.) nutrient agar (Difco) in a 25×100 mm petri plate. Once the agar had cooled and solidified, the petri plate was inverted and incubated at 30° C. for 2 to 5 days. For a particular sample, the petri plate at the serial dilution showing 30 to 300 colonies was selected for enumeration and counted on a Quebec darkfield colony counter using a mechanical hand tally. Using this method, one colony on the agar plate represents one bacterium per ml from the corresponding dilution stock. For total bacteria per ml for a given mud sample, bacteria/ml=no. colonies×serial dilution. For SRB enumeration, serial dilutions of mud samples were made into 10 ml culture vials containing API RP38 SRB media, incubated at 30° C. for 28 days, then visually examined for number of bottles showing growth.

Mud Preparation

A 5 gallon bucket of XCD polymer drilling fluid was prepared containing:

| | | |
|---|---|---|
| Tap water | 0.95 bbls | (151 liters) |
| FLA (fluid loss additive) | 2 ppb | (5.72 g/l) |
| Caustic | 0.10 ppb | (0.286 g/l) |
| KELCO XCD Polymer | 1.50 ppb | (4.29 g/l) |
| Barite | 59 ppb | (169 g/l) |

The mud was stored at 4° C. immediately after preparation until initiation of the study.

Rheology and Physical Measurements of Mud

At appropriate time points, 250 ml aliquots of mud were collected and stored in 8 oz. (0.237 liter) sample jars at 4° C. until analysis. Rheology measurements were made at 120° C. using a Fann 35A viscometer. Readings were taken at 600, 300, 200, 100, 6, and 3 RPM, as well as an initial (10 sec) and 10 minute gel reading at 3 RPM. API filtrate was measured as to the amount of fluid loss at 100 psi for 30 minutes. The pH of the filtrate was then determined with a Jenco pH Vision 6072 pH meter.

Biocide Preparation

The following biocides at the indicated product concentrations were tested during the study:

TABLE A

| | Biocide Concentrations | |
|---|---|---|
| Name | Chemical | ppm |
| MAGNACIDE 575 | liquid THPS | 100, 200, 400 |
| | solid THPS (from Example 1) | 170, 340, 680 |

Product concentration ranges were selected based on preliminary tests that established the minimum concentration of product necessary to exhibit biocidal activity.

Test Procedure

1. On day 0, XCD polymer was distributed to ½ gallon (1.89 liter) test jars in 2000 g aliquots. Prior to inoculation, the mud was allowed to equilibrate to room temperature.

2. Appropriate concentrations of appropriate biocide were delivered to each jar, except for the control, and thoroughly mixed.

3. A volume of 1.5 ml of media containing $1.1 \times 10^{10}$ GAB and 15 ml media containing $1.0 \times 10^{12}$ SRB were added to each jar and mixed thoroughly. The final concentration per ml of mud was $5.5 \times 10^5$ for GAB and $10^9$ for SRB.

4. Note: the uninoculated mud contained $<10^1$ GAB/ml and $<10^1$ SRB/ml.

5. The jars were sealed and incubated at 30° C.

6. At sampling times of 0, 1/2, 3, 7, 15, and 22 days, each jar was mixed thoroughly and a 250 ml aliquot was removed for bacterial enumeration and rheological analysis.

7. At day 15, following sample removal, each jar was reinoculated with $10^6$ GAB/ml and $10^6$ SRB/ml to test the response of the respective biocides to bacterial rechallenge.

Results

Bacterial Growth

Figure 1A:
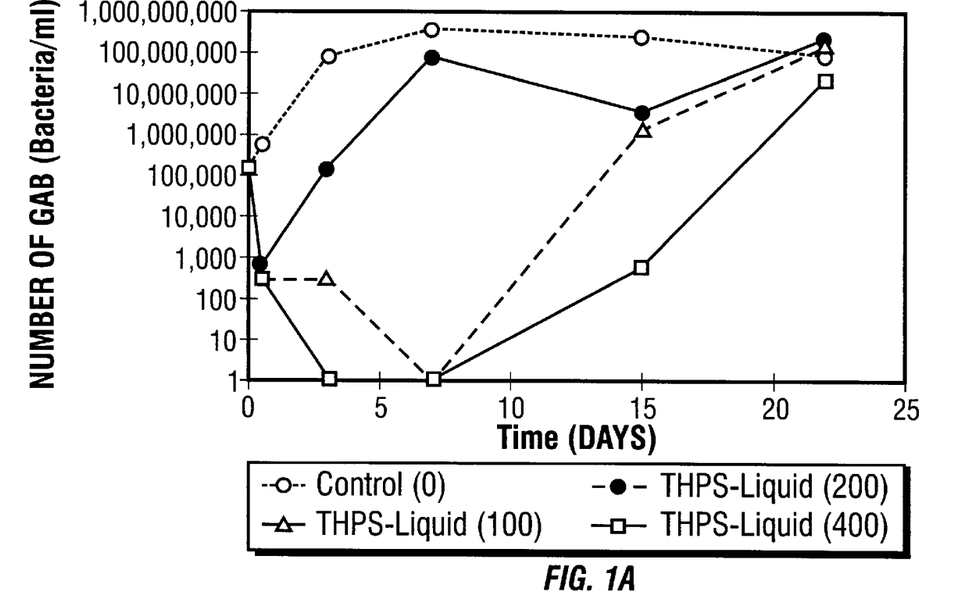
FIG. 1A is a graph of the numbers of general aerobic and facultative anaerobic bacteria (GAB) comparing liquid THPS vs. the control.
Figure 1B:
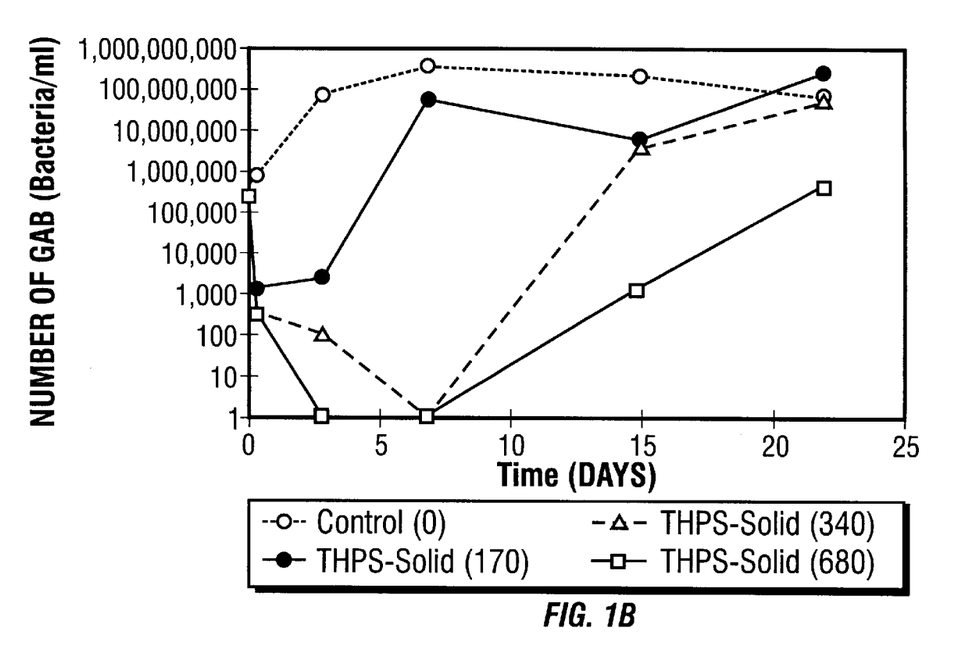
FIG. 1B is a graph of the numbers of GAB comparing solid THPS vs. the control.

All data regarding bacterial counts during the 3 week evaluation of biocide performance in drilling mud is presented in Tables 1–2 and FIGS. 1(A & B) and 2(A & B).

Pour plate counts indicated that the day 0 control GAB population in XCD polymer was established at $1.70 \times 10^5$ bacterial/ml. By day 7, the number of control mud GAB had peaked at $3.35 \times 10^8$ bacterial/ml. The control GAB population had begun to decline by two weeks, presumably due to exhaustion of nutrients, and continued to decrease to $7.40 \times 10^7$ bacteria/ml at day 22. The lower concentration of solid THPS (170 ppm) was not quite as effective as the liquid form, but did result in a 2 log reduction of GAB within 12 hours. By 3 days, mud treated with 100 ppm liquid THPS or 170 ppm solid THPS began to exhibit GAB growth which exceeded $10^7$ bacteria/ml by 7 days. Liquid THPS at 200–400 ppm, and solid THPS at 340–680 ppm maintained low to undetectable GAB levels for up to one week. The liquid THPS at 400 ppm and solid THPS at 680 ppm continued to suppress bacterial growth at 2 weeks. At 3 weeks, following bacterial rechallenge, even the 400 ppm liquid or 680 ppm solid THPS failed to control GAB growth.

Figure 2A:
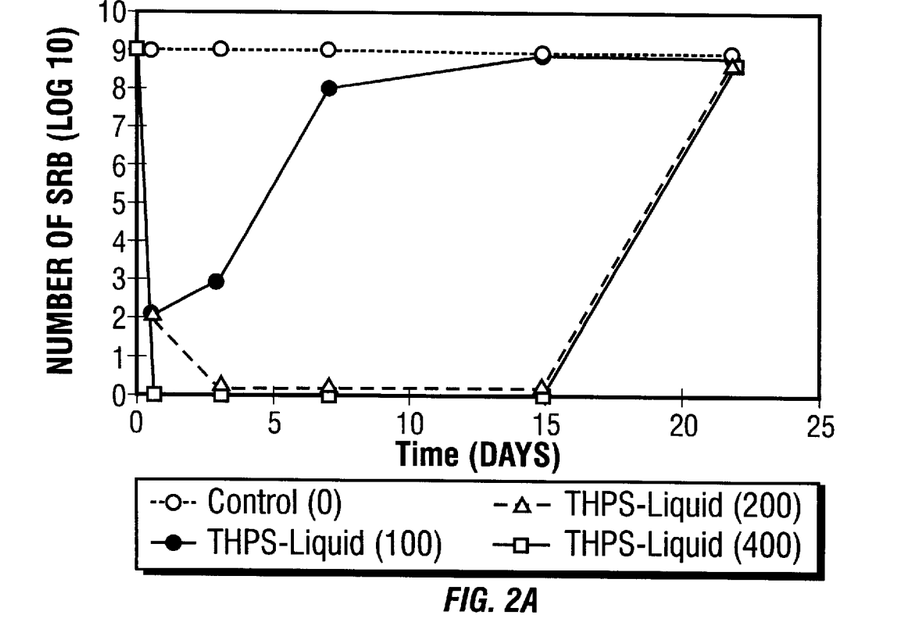
FIG. 2A is a graph of the numbers of sulfate reducing bacteria (SRB) comparing liquid THPS vs. the control.
Figure 2B:
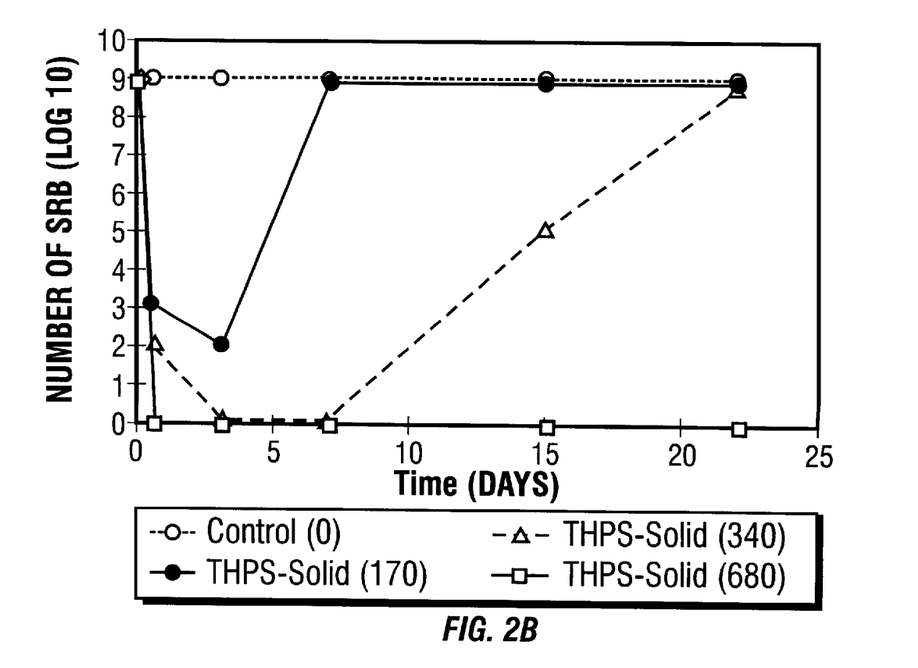
FIG. 2B is a graph of the numbers of SRB comparing solid THPS vs. the control.

Examination of the SRB serially diluted culture vials indicated that the control day 0 SRB population was established at $10^9$ bacteria/ml. Both solid and liquid THPS at all concentrations exhibited quick killing tendencies. In fact, 400 ppm liquid THPS and 680 ppm solid THPS reduced the SRB population to $<10^1$ bacteria/ml, below the detection limit. Solid THPS at 680 ppm maintained the SRB levels below detection limit for the remainder of the study. Solid THPS at 340 ppm allowed a resurgence in bacterial growth to $10^5$ bacteria/ml at day 15, further increasing to $10^9$ bacteria/ml at day 22. Liquid THPS at 200 and 400 ppm maintained the SRB counts below detection until day 22 at which point the number of SRB jumped to $10^9$ bacteria/ml.

TABLE 1

Numbers of General Aerobic and Facultative Anaerobic Bacteria

| Biocide | Conc. (ppm) | Time (days) | | | | | |
|---|---|---|---|---|---|---|---|
| | | 0 | 0.5 | 3 | 7 | 15* | 22 |
| Control | 0 | $1.70 \times 10^5$ | $5.80 \times 10^5$ | $7.00 \times 10^7$ | $3.35 \times 10^8$ | $2.19 \times 10^8$ | $7.40 \times 10^7$ |
| THPS -Liquid | 100 | $1.70 \times 10^5$ | $7.00 \times 10^2$ | $1.40 \times 10^5$ | $6.9 \times 10^7$ | $3.14 \times 10^6$ | $1.86 \times 10^8$ |
| | 200 | $1.70 \times 10^5$ | $3.00 \times 10^2$ | $3.00 \times 10^2$ | 0 | $1.23 \times 10^6$ | $1.61 \times 10^8$ |
| | 400 | $1.70 \times 10^5$ | $3.00 \times 10^2$ | 0 | 0 | $6.00 \times 10^2$ | $2.00 \times 10^7$ |
| THPS -Solid | 170 | $1.70 \times 10^5$ | $1.30 \times 10^3$ | $2.00 \times 10^3$ | $5.20 \times 10^7$ | $6.00 \times 10^6$ | $2.88 \times 10^8$ |
| | 340 | $1.70 \times 10^5$ | $3.00 \times 10^2$ | $1.00 \times 10^2$ | 0 | $4.00 \times 10^6$ | $6.20 \times 10^7$ |
| | 680 | $1.70 \times 10^5$ | $3.00 \times 10^2$ | 0 | 0 | $1.30 \times 10^3$ | $4.70 \times 10^5$ |

*reinoculation

TABLE 2

Numbers of Sulfate-Reducing Bacteria
(expressed as log 10)

| Biocide | Conc. (ppm) | 0 | 0.5 | 3 | 7 | 15* | 22 |
|---|---|---|---|---|---|---|---|
| Control | — | 9 | 9 | 9 | 9 | 9 | 9 |
| THPS -Liquid | 100 | 9 | 2 | 3 | 8 | 9 | 9 |
|  | 200 | 9 | 2 | 0 | 0 | 0 | 9 |
|  | 400 | 9 | 0 | 0 | 0 | 0 | 9 |
| THPS -Solid | 170 | 9 | 3 | 2 | 9 | 9 | 9 |
|  | 340 | 9 | 2 | 0 | 0 | 5 | 9 |
|  | 680 | 9 | 0 | 0 | 0 | 0 | 0 |

*reinoculation

Rheology

As mentioned, the xanthan gum in XCD drilling fluid is highly sensitive to microbial degradation. In the untreated control, it was visually apparent by 3 days that the physical properties of the mud had changed. This was evidenced by separation of the water from the mud as well as change in color from light tan to dark gray. These changes are clearly reflected in the following data.

pH Data

Figure 3A:
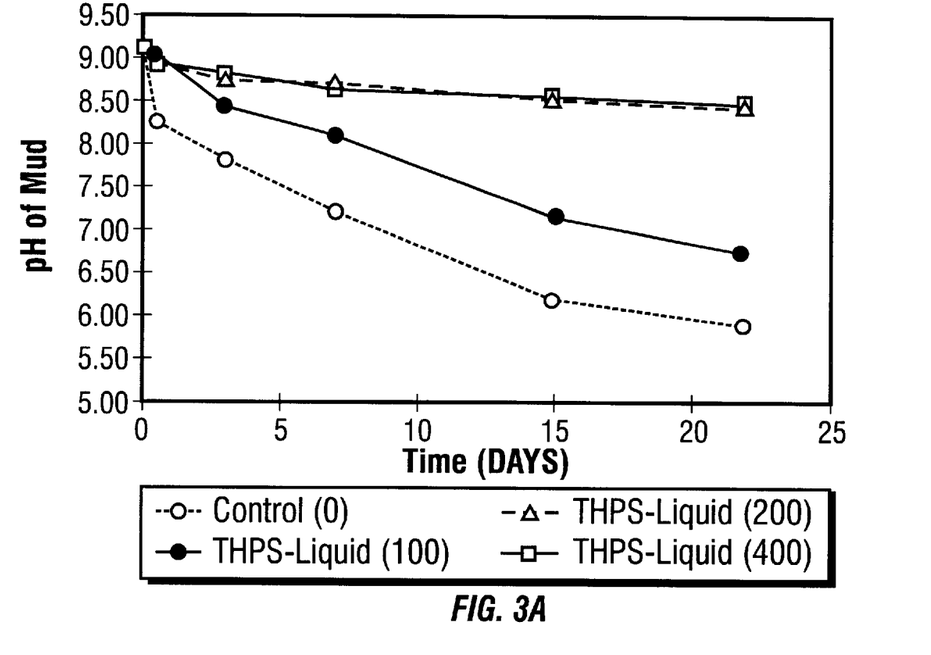
FIG. 3A is a graph of the pH of the mud comparing liquid THPS vs. the control.
Figure 3B:
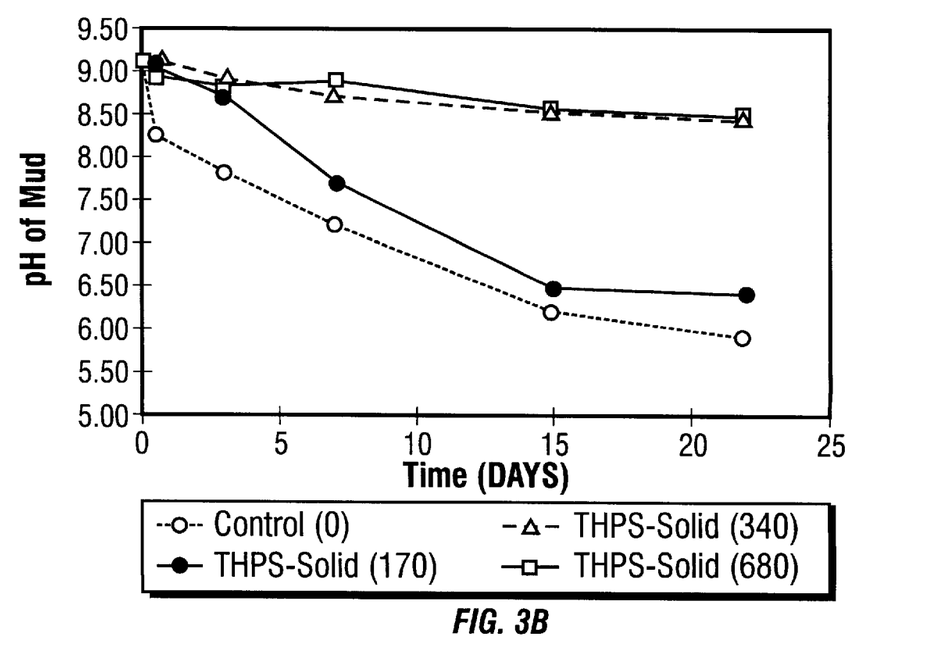
FIG. 3B is a graph of the pH of the mud comparing solid THPS vs. the control.

The pH data can be found in Table 3 and is graphically represented in FIGS. 3A and 3B.

The initial pH of XCD drilling fluid was 9.10. During the 22 day period of the study, there was a continual decrease in pH of the inoculated control mud, beginning as early as 12 hours following inoculation with a downshift to pH 8.25 and concluding at day 22 with a pH of 5.87. This shift to acidic pH in the control mud can be mostly attributed to the metabolic action of bacteria on the xanthan gum polymer. As the polymer breaks down, bacteria utilize the simple sugars producing small chain organic acids. The accumulation of organic acids in the mud causes a decrease in pH.

THPS was an effective biocide at preventing large pH changes in the inoculated mud. Liquid THPS at 200–400 ppm and solid THPS at 320–680 ppm minimized pH changes in the inoculated mud to slightly over half a pH unit. At less than these concentration rages for liquid or solid THPS, the pH was not stable and decreased a full unit by the first week of the study, continuing to fall well below 7 by day 22.

TABLE 3 pH Data

| Biocide | Conc. (ppm) | 0 | 0.5 | 3 | 7 | 15* | 22 |
|---|---|---|---|---|---|---|---|
| Control | — | 9.10 | 8.25 | 7.79 | 7.187 | 6.17 | 5.87 |
| THPS -Liquid | 100 | 9.10 | 9.03 | 8.42 | 8.09 | 7.13 | 6.70 |
|  | 200 | 9.10 | 8.92 | 8.73 | 8.70 | 8.52 | 8.45 |
|  | 400 | 9.10 | 8.92 | 8.82 | 8.64 | 8.55 | 8.47 |
| THPS -Solid | 170 | 9.10 | 9.00 | 8.65 | 7.67 | 6.48 | 6.42 |
|  | 340 | 9.10 | 9.10 | 8.88 | 8.67 | 8.53 | 8.43 |
|  | 680 | 9.10 | 8.97 | 8.80 | 8.87 | 8.59 | 8.54 |

*reinoculation

API Filtrate

Figure 4A:
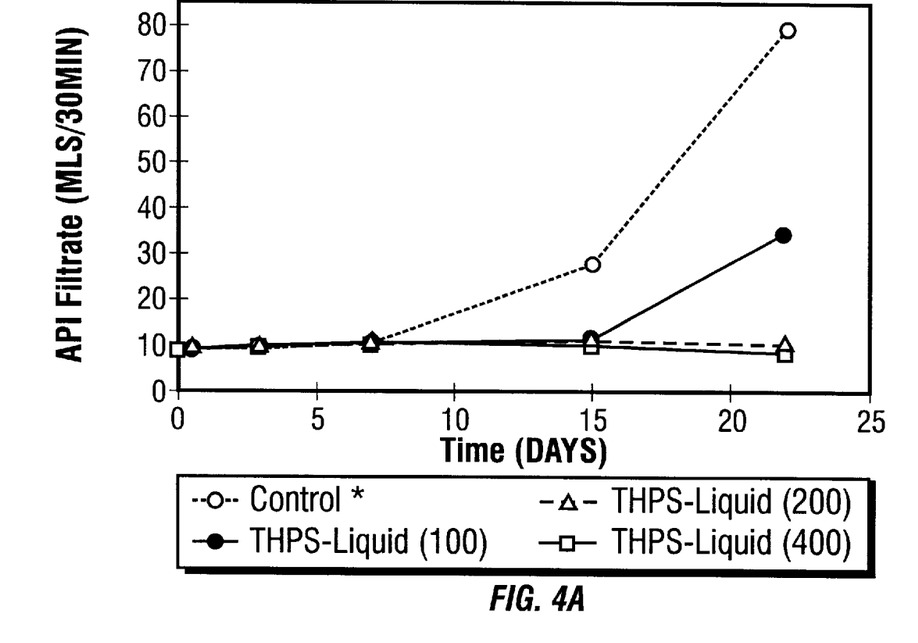
FIG. 4A is a graph of the API filtrate comparing liquid THPS vs. the control.
Figure 4B:
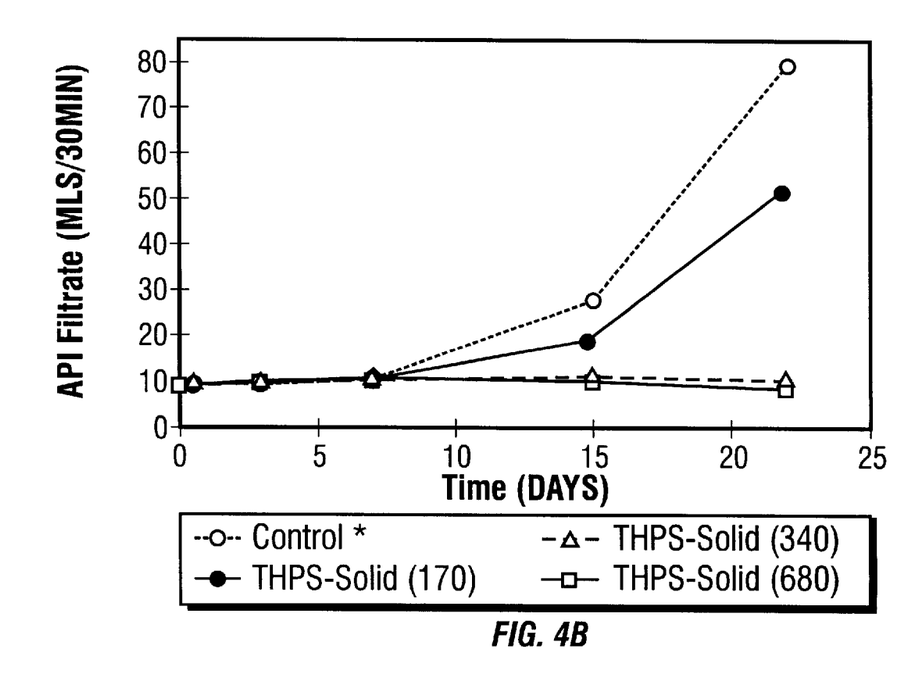
FIG. 4B is a graph of the API filtrate comparing solid THPS vs. the control.
Figure 5A:
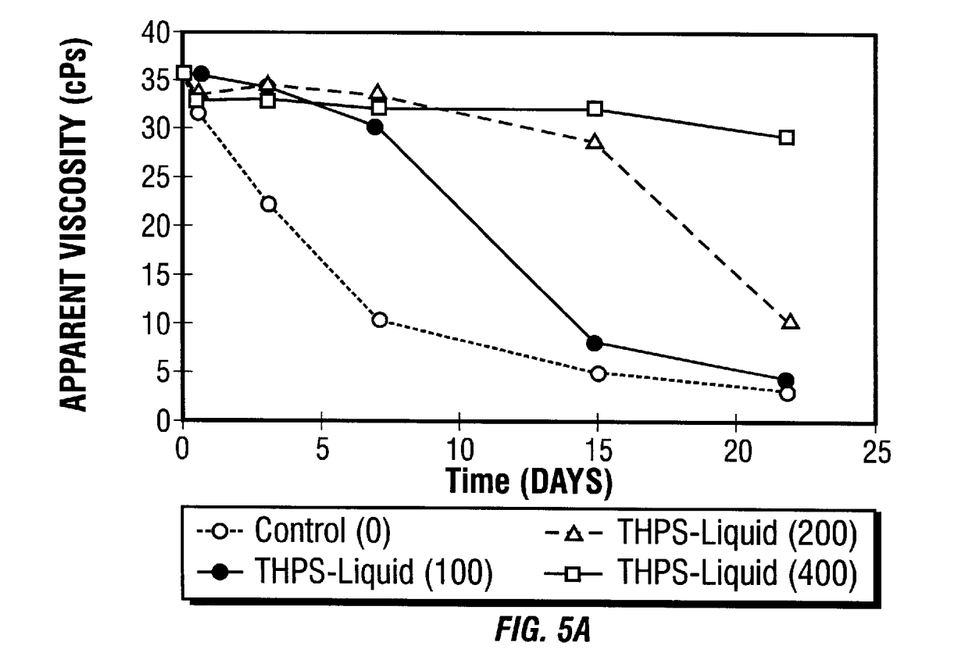
FIG. 5A is a graph of the apparent viscosity (AP) comparing liquid THPS vs. the control.
Figure 5B:
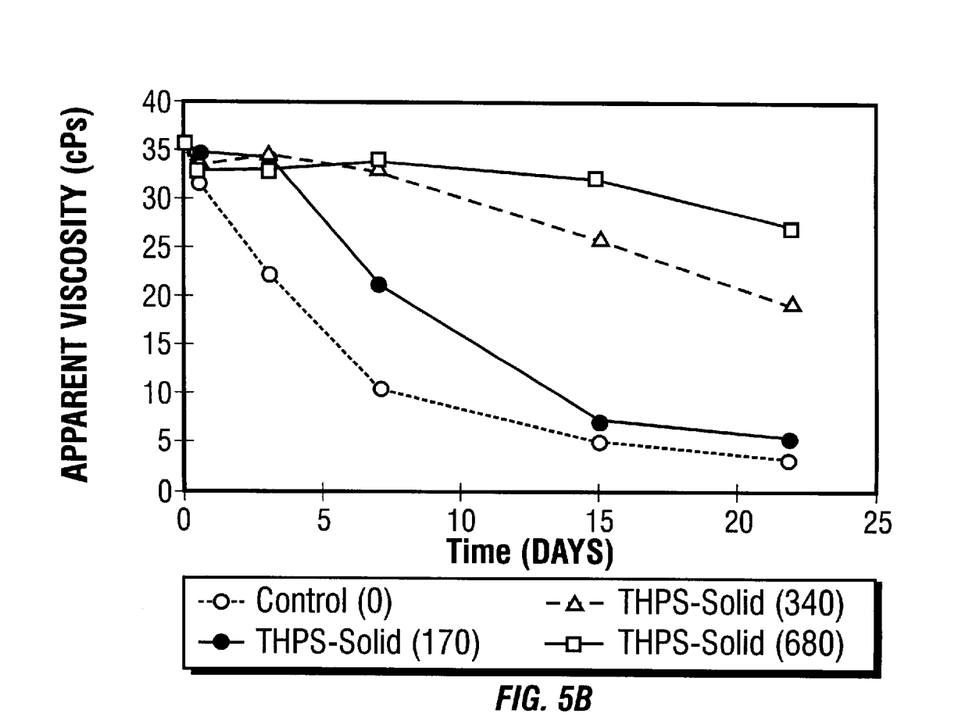
FIG. 5B is a graph of the apparent viscosity (AP) comparing solid THPS vs. the control.
Figure 6A:
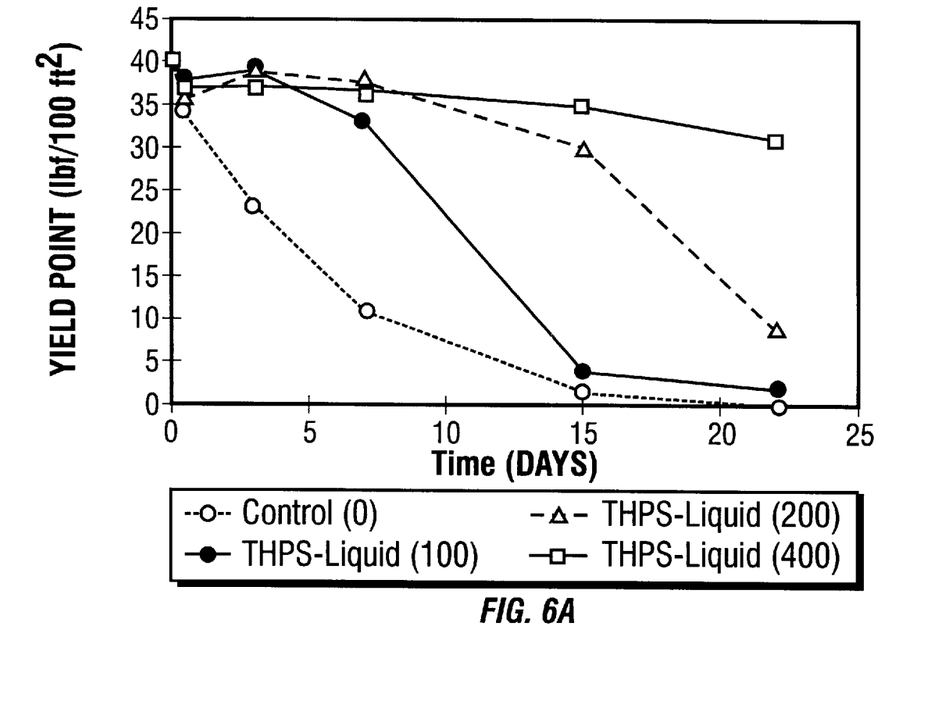
FIG. 6A is a graph of the yield point (YP) comparing liquid THPS vs. the control.
Figure 6B:
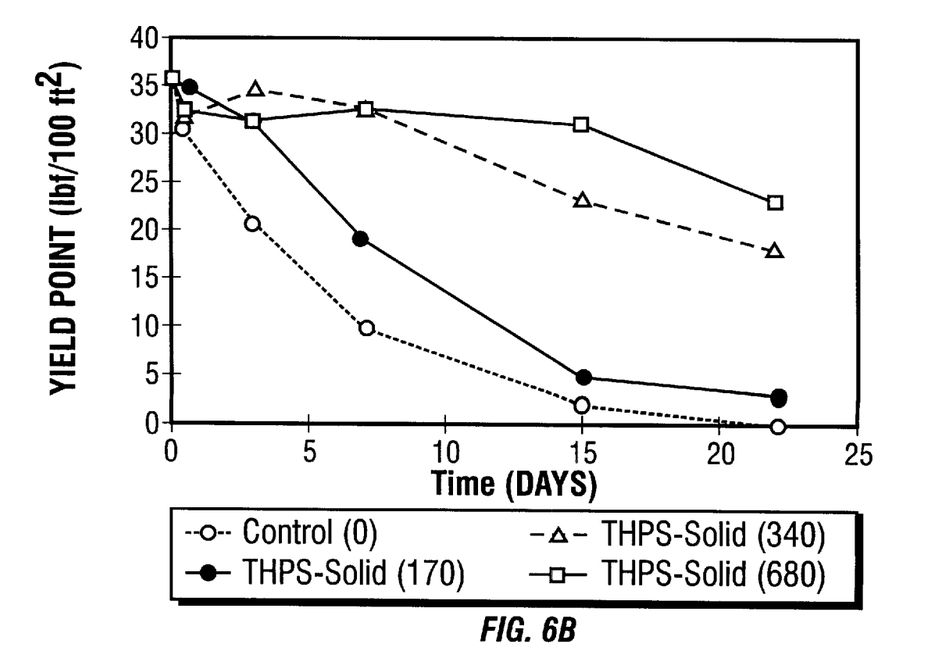
FIG. 6B is a graph of the yield point (YP) comparing solid THPS vs. the control.
Figure 7A:
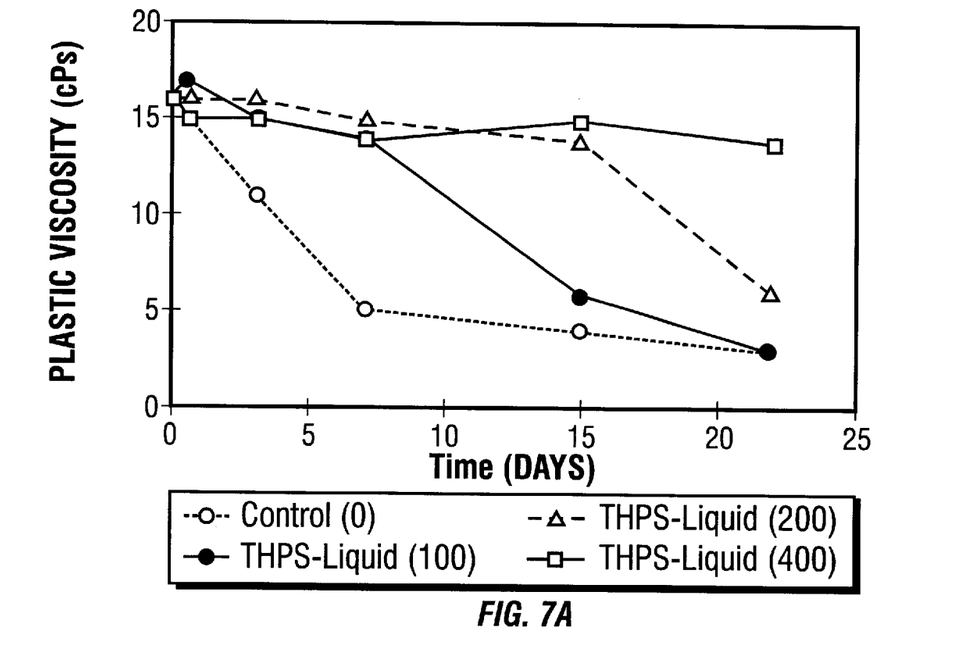
FIG. 7A is a graph of the plastic viscosity (PV) comparing liquid THPS vs. the control.
Figure 7B:
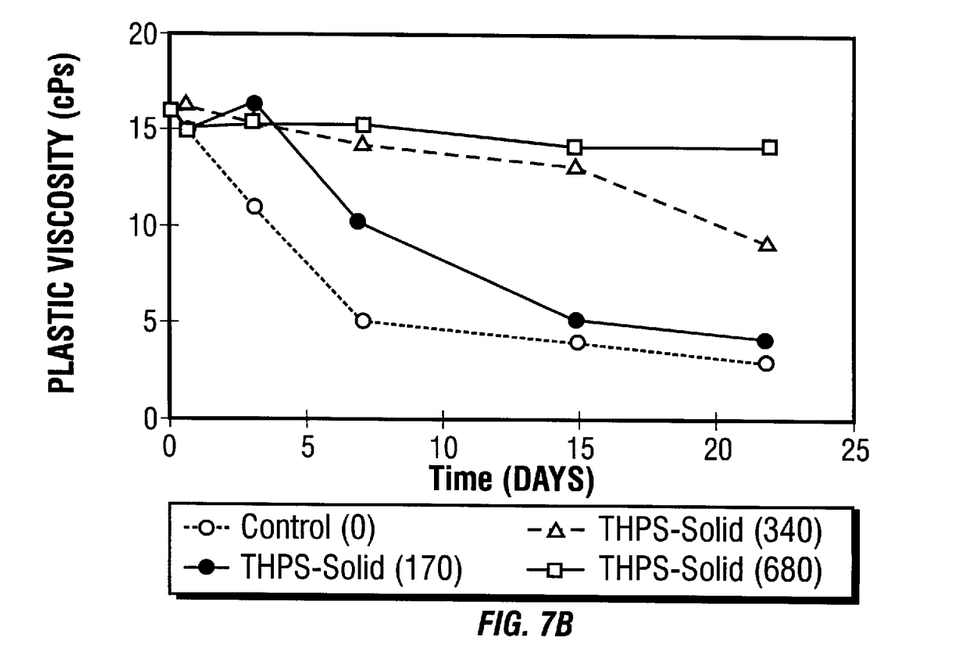
FIG. 7B is a graph of the plastic viscosity (PV) comparing solid THPS vs. the control.
Figure 8A:
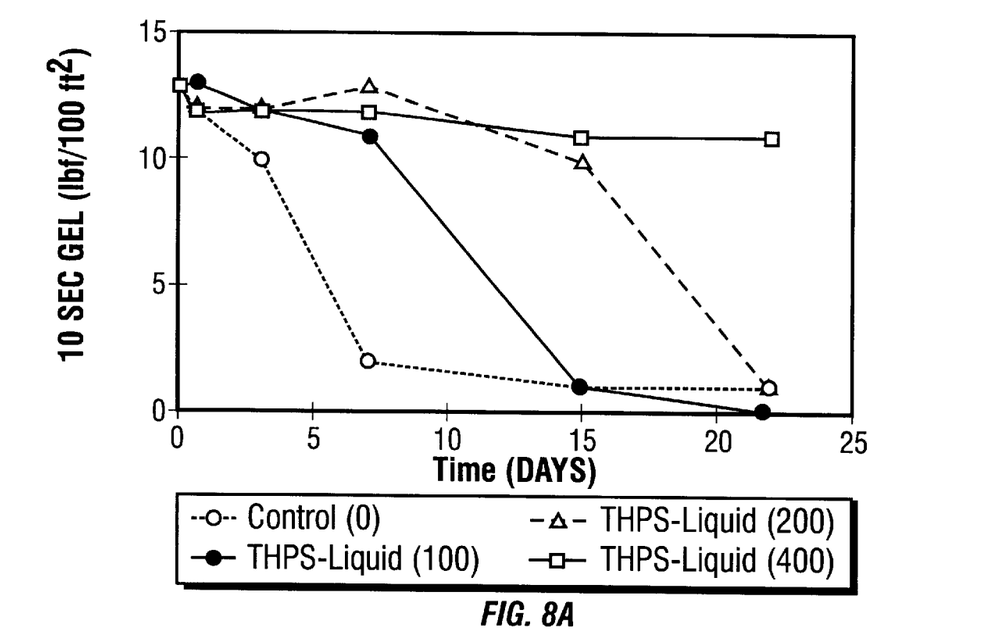
FIG. 8A is a graph of the initial gel comparing liquid THPS vs. the control.
Figure 8B:
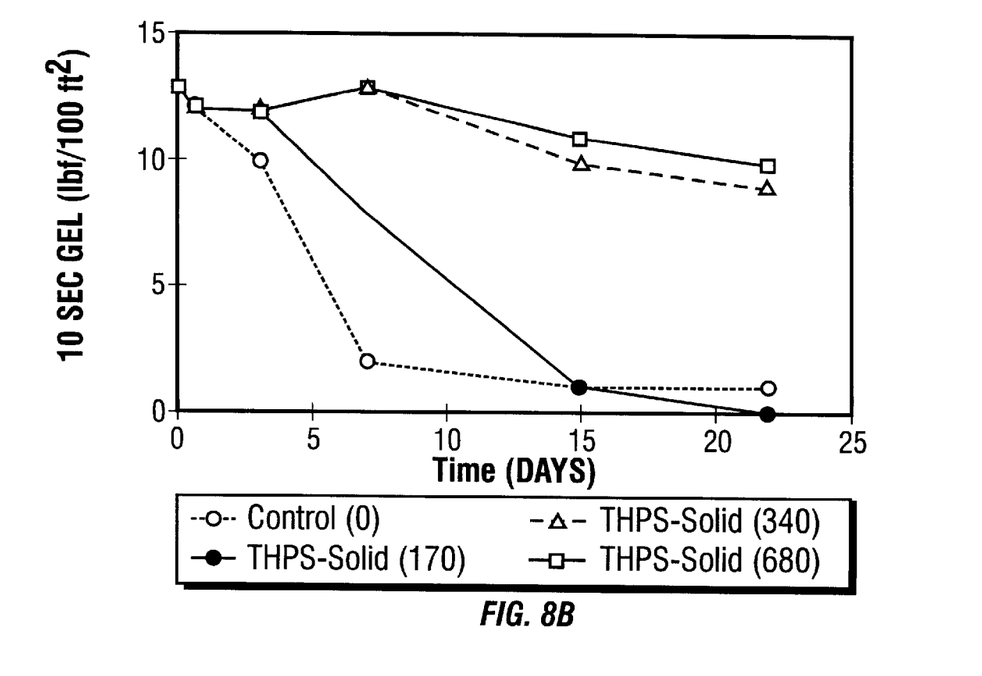
FIG. 8B is a graph of the initial gel comparing solid THPS vs. the control.
Figure 9A:
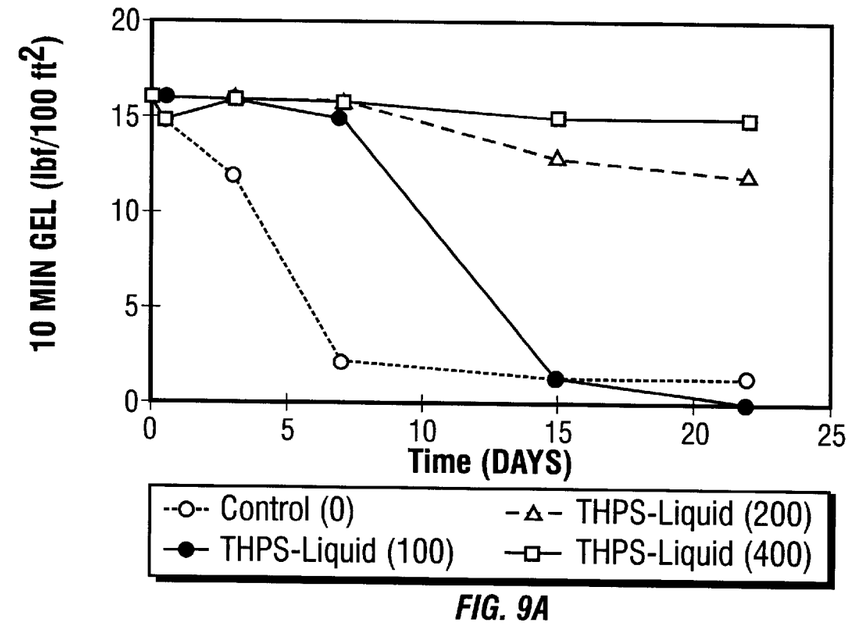
FIG. 9A is a graph of the 10 minute gel comparing liquid THPS vs. the control.
Figure 9B:
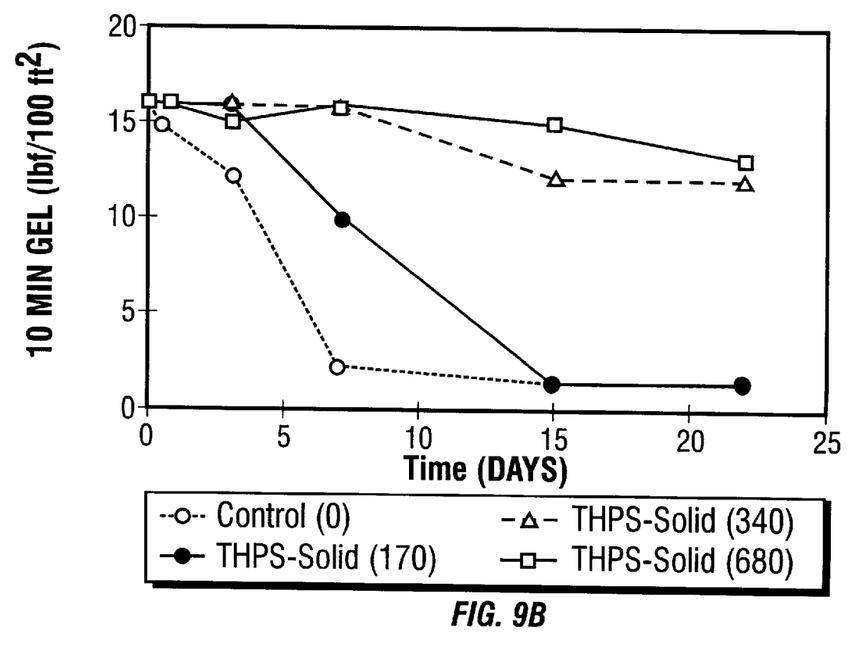
FIG. 9B is a graph of the 10 minute gel comparing solid THPS vs. the control.

The API filtrate data is presented in Table 4 and FIGS. 4A and 4B.

In general, all mud samples were relatively stable to increases in fluid loss following bacterial contamination for up to one week. The inoculated control mud showed less than a 2 ml increase in API filtrate, from an initial 8.4 ml to 10.0 ml during the first week of incubation. By day 15, however, the filtrate loss in the control mud was substantial, increasing to 28 ml. By the end of the study, the filtrate loss by the inoculated control mud was 80 ml.

Liquid THPS at 200–400 ppm and solid THPS at 340–680 ppm preserved increases in fluid loss from XCD polymer under conditions of bacterial inoculation. A maximum increase of <2 ml in API filtrate was measured among these samples from the initial loss of 8.4 ml at day 0 to 9–10 ml at day 22.

TABLE 4

API Filtrate (mls/30 minutes)

| Biocide | Conc. (ppm) | 0 | 0.5 | 3 | 7 | 15* | 22 |
|---|---|---|---|---|---|---|---|
| Control | — | 8.4 | 8.4 | 8.8 | 10.0 | 28.0 | 80.0 |
| THPS -Liquid | 100 | 8.4 | 9.2 | 10.0 | 10.0 | 11.5 | 35.0 |
|  | 200 | 8.4 | 9.6 | 9.2 | 10.0 | 11.5 | 9.5 |
|  | 400 | 8.4 | 9.0 | 9.4 | 10.5 | 11.5 | 9.0 |
| THPS -Solid | 170 | 8.4 | 8.6 | 10.2 | 12.0 | 20.0 | 54.0 |
|  | 340 | 8.4 | 8.8 | 9.7 | 11.5 | 11.5 | 10.0 |
|  | 680 | 8.4 | 8.3 | 10.0 | 10.5 | 11.0 | 9.5 |

*reinoculation

Apparent Viscosity, Plastic Viscosity, and Yield Point

During the course of the study, the mud samples were measured for the laminar flow properties: apparent viscosity (AV), plastic viscosity (PV), and yield point (YP). These data are presented in Tables 5–7 and FIGS. 5A, 5B, 6A, 6B, 7A and 7B.

Upon examination of the laminar flow data, it is apparent that the decreases in AP, PV, and YP in contaminated mud samples over the course of the study are reflective of increases in bacterial numbers observed in Table 1 and FIGS. 1A and 1B. The inoculated control mud underwent complete degradation with respect to its physical properties. Decreases in the AV and YP of the control mud were evident by 12 hours. By day 3, AV, YP and PV of the control mud were dramatically reduced. This finding correlated with changes in the appearance of the control mud, which separated into an extensive water layer overlying a mud-like layer.

Liquid THPS at 400 ppm, and to a lesser degree solid THPS at 680 ppm, were able to approximately preserve the rheological properties of XCD polymer following bacterial inoculation. Relatively minimal decreases in AV, YP and PV were observed over the course of the study. Liquid THPS at 200 ppm, and solid THPS at 340 ppm, were able to maintain the integrity of the XCD mud for 15 days.

TABLE 5

Apparent Viscosity (cPs)

| Biocide | Conc. (ppm) | 0 | 0.5 | 3 | 7 | 15* | 22 |
|---|---|---|---|---|---|---|---|
| Control | — | 36 | 32 | 23 | 11 | 5 | 3 |
| THPS -Liquid | 100 | 36 | 36 | 35 | 31 | 8 | 4 |
|  | 200 | 36 | 36 | 35 | 31 | 8 | 4 |
|  | 400 | 36 | 34 | 34 | 33 | 33 | 30 |
| THPS -Solid | 170 | 36 | 35 | 34 | 21 | 8 | 6 |
|  | 340 | 36 | 34 | 35 | 33 | 26 | 19 |
|  | 680 | 36 | 33 | 33 | 34 | 32 | 27 |

*reinoculation

TABLE 6

Yield Point (lbf/100 ft²)

| Biocide | Conc. (ppm) | 0 | 0.5 | 3 | 7 | 15* | 22 |
|---|---|---|---|---|---|---|---|
| Control | — | 40 | 34 | 23 | 11 | 2 | 0 |
| THPS -Liquid | 100 | 40 | 48 | 39 | 33 | 4 | 2 |
|  | 200 | 40 | 36 | 38 | 38 | 30 | 9 |
|  | 400 | 40 | 37 | 37 | 37 | 35 | 31 |
| THPS -Solid | 170 | 40 | 39 | 35 | 21 | 5 | 3 |
|  | 340 | 40 | 36 | 39 | 37 | 26 | 20 |
|  | 680 | 4 | 36 | 35 | 37 | 35 | 26 |

*reinoculation

TABLE 7

Plastic Viscosity (cPs)

| Biocide | Conc. (ppm) | 0 | 0.5 | 3 | 7 | 15* | 22 |
|---|---|---|---|---|---|---|---|
| Control | — | 16 | 15 | 11 | 5 | 4 | 3 |
| THPS -Liquid | 100 | 16 | 17 | 15 | 14 | 6 | 3 |
|  | 200 | 16 | 16 | 16 | 15 | 14 | 6 |
|  | 400 | 16 | 15 | 15 | 14 | 15 | 14 |
| THPS -Solid | 170 | 16 | 15 | 16 | 10 | 5 | 4 |
|  | 340 | 16 | 16 | 15 | 14 | 13 | 9 |
|  | 680 | 16 | 15 | 15 | 15 | 14 | 14 |

*reinoculation

Gel Strength

Measurements of the initial (10 sec.) and 10 minute gel strengths of the sample muds are presented in Tables 8–9 and FIGS. 8A, 8B, 9A, and 9B.

As observed with the other rheological properties, Liquid THPS at 400 ppm and solid THPS at 680 ppm were generally maintained the integrity of the XCD gel strength for the duration of the performance study. Liquid THPS at 200 ppm solid THPS at 340 ppm also maintained gel strength for the entire 3 weeks, although not as effectively as the higher doses.

TABLE 8

Initial Gel Strength (lbf/100 ft²)

| Biocide | Conc. (ppm) | 0 | 0.5 | 3 | 7 | 15* | 22 |
|---|---|---|---|---|---|---|---|
| Control | — | 13 | 12 | 10 | 2 | 1 | 1 |
| THPS -Liquid | 100 | 13 | 13 | 12 | 11 | 1 | 0 |
|  | 200 | 13 | 12 | 12 | 13 | 10 | 1 |
|  | 400 | 13 | 12 | 12 | 12 | 11 | 11 |
| THPS -Solid | 170 | 13 | 12 | 12 | 8 | 1 | 0 |
|  | 340 | 13 | 12 | 12 | 13 | 10 | 9 |
|  | 680 | 13 | 12 | 12 | 13 | 11 | 10 |

*reinoculation

TABLE 9

10 Minute Gel Strength (lbf/100 ft²)

| Biocide | Conc. (ppm) | 0 | 0.5 | 3 | 7 | 15* | 22 |
|---|---|---|---|---|---|---|---|
| Control | — | 16 | 15 | 12 | 2 | 1 | 1 |
| THPS -Liquid | 100 | 16 | 16 | 16 | 15 | 1 | 0 |
|  | 200 | 16 | 15 | 16 | 16 | 13 | 12 |
|  | 400 | 16 | 15 | 16 | 16 | 15 | 15 |
| THPS -Solid | 170 | 16 | 16 | 16 | 10 | 1 | 1 |
|  | 340 | 16 | 16 | 16 | 16 | 12 | 12 |
|  | 680 | 16 | 16 | 15 | 16 | 15 | 13 |

*reinoculation

As demonstrated, a rigorous test of biocide performance in drilling fluids was conducted using XCD polymer as the test drilling fluid. XCD polymer was selected because it is highly conducive to bacterial growth. Inoculation of this drilling fluid with $10^5$ GAB/ml and $10^9$ SRB/ml destroyed its physical integrity within 3 days. Liquid THPS and solid THPS performed effectively as quick killing biocides, decreasing the GAB and SRB populations dramatically within 12 hours. However, neither biocide was able to maintain long term control as the bacterial populations achieved $10^8$ GAB/ml and $10^9$ SRB/ml by the end of the 22 day study. The surprising exception to this loss of control was the 680 ppm solid THPS, which suppressed GAB growth to $10^5$ and SRB growth to below detectable levels until the end of the study. It is noteworthy that THPS in solid or liquid form was by far the most effective biocide against SRB.

In the foregoing specification, the invention has been described with reference to specific embodiments thereof, and has been demonstrated as effective in controlling bacteria in oil field fluids, e.g. drilling fluids, as a non-limiting example. However, it will be evident that various modifications and changes can be made thereto without departing from the broader spirit or scope of the invention as set forth in the appended claims. Accordingly, the specification is to be regarded in an illustrative rather than a restrictive sense. For example, specific substrates, proportions of THPS on the substrate, and combinations thereof, other than those specifically tried, falling within the claimed parameters, but not specifically identified or tried in a particular application to control bacteria, are within the scope of this invention. Similarly, it is expected that the inventive dry form of THPS will find utility as a biocide in other fluids and solids besides those specifically tried herein.

We claim:

1. A method of inhibiting bacterial growth in compositions selected from the group consisting of fluids and solids comprising adding thereto an effective bacterial inhibiting amount of a biocide comprising tetra-kis-hydroxymethyl-phosphonium sulfate (THPS) adsorbed on a solid, particulate, flowable substrate selected from the group consisting of silica, sodium sulfate, sodium carbonate, sodium chloride, potassium chloride, and borax.

2. The method of claim 1 where the THPS is sprayed onto the solid, particulate substrate.

3. The method of claim 1 where the solid, particulate substrate is silica.

4. A dry biocide comprising tetra-kis-hydroxymethyl-phosphonium sulfate (THPS) adsorbed on a solid, particulate, flowable substrate selected from the group consisting of silica, sodium sulfate, sodium carbonate, sodium chloride, potassium chloride, and borax.

5. The dry biocide of claim 4 where the dry biocide is made by the process of spraying THPS onto the solid, particulate substrate.

6. The dry biocide of claim 4 where the solid, particulate substrate is silica.

7. The dry biocide of claim 4 where the proportion of THPS on the substrate ranges from about 1 to about 90 wt %.

8. A composition inhibited against bacterial growth comprising
   a composition selected from the group consisting of fluids and solids; and
   an effective bacterial inhibiting amount of a biocide comprising tetra-kis-hydroxymethyl-phosphonium sulfate (THPS) adsorbed on a solid, particulate, flowable substrate selected from the group consisting of silica, sodium sulfate, sodium carbonate, sodium chloride, potassium chloride, and borax.

9. The fluid of claim 8 where the solid, particulate substrate is silica.

10. A method for producing a dry biocide comprising spraying tetra-kis-hydroxymethyl-phosphonium sulfate (THPS) onto a solid, particulate, flowable substrate for adsorption thereon where the substrate is selected from the group consisting of silica, sodium sulfate, sodium carbonate, sodium chloride, potassium chloride, and borax.

11. The method of claim 10 where the THPS is sprayed such that it becomes an aerosol before it contacts the solid, particulate substrate.

12. The method of claim 10 where the solid, particulate substrate is silica.

* * * * *

UNITED STATES PATENT AND TRADEMARK OFFICE
CERTIFICATE OF CORRECTION

PATENT NO. : 6,001,158
DATED : December 14, 1999
INVENTOR(S) : Eugene A. Elphingstone et al.

It is certified that error appears in the above-identified patent and that said Letters Patent is hereby corrected as shown below:

At column 9, line 40, after the phrase 200 ppm, please insert -- and --.

Signed and Sealed this

Eighth Day of August, 2000

Attest:

Attesting Officer

Q. TODD DICKINSON
Director of Patents and Trademarks